(12) United States Patent
Zhang et al.

(10) Patent No.: US 7,355,080 B2
(45) Date of Patent: Apr. 8, 2008

(54) METHOD OF PREPARING MEMANTINE HYDROCHLORIDE

(75) Inventors: Fuli Zhang, Shanghai (CN); Meng Hu, Shanghai (CN); Lizhi Zhao, Shanghai (CN); Mengya Ge, Hengdian Dongyang (CN)

(73) Assignees: Shanghai Institute of Pharmaceutical Industry, Shanghai (CN); Zhejiang Kangyu Pharmaceutical Co., Ltd., Dongyang (CN)

( * ) Notice: Subject to any disclaimer, the term of this patent is extended or adjusted under 35 U.S.C. 154(b) by 0 days.

(21) Appl. No.: 10/575,948

(22) PCT Filed: Dec. 19, 2003

(86) PCT No.: PCT/CN03/01094

§ 371 (c)(1),
(2), (4) Date: Oct. 17, 2006

(87) PCT Pub. No.: WO2005/023753

PCT Pub. Date: Mar. 17, 2005

(65) Prior Publication Data

US 2007/0078283 A1    Apr. 5, 2007

(30) Foreign Application Priority Data

Sep. 10, 2003  (CN)  ................. 03 1 50892

(51) Int. Cl.
*C07C 209/00* (2006.01)
(52) U.S. Cl. ...................................... 564/445
(58) Field of Classification Search ............... None
See application file for complete search history.

(56) References Cited

U.S. PATENT DOCUMENTS 4,122,193 A  10/1978  Sherm et al.
5,061,703 A  10/1991  Bormann et al.

FOREIGN PATENT DOCUMENTS

CN  1335299 A  2/2002
CN  1400205 A  3/2003

*Primary Examiner*—Samuel Barts
(74) *Attorney, Agent, or Firm*—Crowell & Moring LLP

(57) ABSTRACT

A new method of preparing memantine hydrochloride, comprising the following steps: reacting 1-bromo-3,5-dimethyl adamantane and urea/formic acid, with formic acid also acting as the solvent; hydrolyzing with aqueous inorganic acid; alkalifying, extracting and acidifying with hydrochloric acid; finally collecting target compound. The method uses inexpensive raw materials and is performed in homogeneous phase under mild conditions. It can achieve high yield and good product purity, and is suitable for macrochemistry. The purity of crude product is 99.0%, and reaches 99.98% after first recrystallization, yield: 69.5%, mp: 332 C (DSC).

12 Claims, 1 Drawing Sheet

METHOD OF PREPARING MEMANTINE HYDROCHLORIDE

CROSS-REFERENCE TO RELATED APPLICATIONS

This application is a 371(c) National Stage of PCT/CN2003/001094 filed Dec. 19, 2003 which claims priority to Chinese patent application Serial No. CN 03150892.8 filed Sep. 10, 2003, the disclosures of which are hereby incorporated by reference in their entireties.

FIELD OF THE INVENTION

This invention relates to a synthesis method for Memantine Hydrochloride, which is a drug for the treatment of moderate to severe Alzheimer's disease (AD).

TECHNICAL BACKGROUND

Memantine Hydrochloride of Merz-Germany became available in 1982 and is still used for treatment of Parkinson's disease, Neuropathic Myotonia and Dementia Syndrome. The drug is sold under the trade name Akatinol in a few countries such as Germany. Memantine Hydrochloride was previously found to act as NMDA (N-methyl-D-aspartate) receptor antagonist. Now, Memantine Hydrochloride has been approved as an effective drug for the treatment of moderate to severe AD by the European Union and it has become the first approved drug for the treatment of moderate to severe AD. In USA, the phase III clinical study has been completed and a NDA has been submitted to FDA. Because there is no effective medicine for the treatment of moderate to severe AD, Memantine Hydrochloride is of great interest. The drug has profound potential as a medicine for treating moderate to severe Vascular Dementia. This condition is also without an effective treatment.

With regard to the synthesis of Memantine Hydrochloride, there are two method reported in the literature, one is U.S. Pat. No. 3,391,142 using acetonitrile/sulfuric acid and the other is U.S. Pat. No. 4,122,193 using urea in the synthesis.

In the method of U.S. Pat. No. 3,391,142, 1,3-dimethyl adamantane is bromized to yield 1-bromo-3,5-dimethyl adamantane, which is then subjected to acetylation and ammonization in the presence of acetonitrile and sulfuric acid, extracted with benzene, dried and concentrated to yield 1-acetamino-3,5-dimethyl adamantane. After the alcoholysis with sodium hydroxide and diethylene glycol, extraction in benzene and concentration, memantine crude was obtained, which was then salified with hydrochloric acid, re-crystallize with ethanol/ether and purified to yield Memantine Hydrochloride.

This method uses acetonitrile, benzene and ether, which are hazardous to environment and human, in the process of acetylation, ammonization and re-crystallization. Furthermore, this method is difficult to hydrolyze acetyl compound, produces many by-products and darkens the product due to the reaction of long duration. It is difficult with this method to meet the purity standards for pharmaceutical use. Therefore, it is necessary to improve this method.

The method of U.S. Pat. No. 4,122,193 uses 1-bromo-3,5-dimethyl adamantane as the raw material, which reacts with urea at 220° C. in tube sealing to yield agglomerate product. The product is milled and mixed with water into mash, then acidified to adjust pH between 3 and 5. Impurities are removed by ether extraction. The aqueous layer is basified to a pH of between 12 and 13. After extracted with ether several times, the organic layers is combined, dried, salified by inletting HCl gas to yield Memantine Hydrochloride. This method adopts tube sealing, and the high reaction temperature may cause the agglomeration of product. As a result, it is difficult industrialize this method.

DESCRIPTION OF THE INVENTION

This invention aims to develop a new preparation method of Memantine Hydrochloride to overcome the above-mentioned technical limitations and to provide a new process that facilitates the industrialization of this product.

In one embodiment, the invention is as follows:

1-bromo-3,5-dimethyl adamantane is aminated with urea/formic acid, where formic acid is also used as solvent, hydrolyzed with inorganic acid aqueous solution, basified, extracted with solvent, and salified with hydrochloric acid. Then the target product Memantine Hydrochloride is collected.

The detailed preparation method involves the following steps:

1-bromo-3,5-dimethyl adamantane, urea and formic acid react at a molar ratio of 1:0.5~10:1~15 at 50-180° C. for 0.25-5 h. After the reaction, inorganic acid aqueous solution is added. Hydrolyzation is performed at a pH from 1 to 3 at 50-100° C. for 0.5 to 5 h. The pH value of the solution is adjusted with inorganic acid aqueous solution to a pH from 10 to 14. After extracted with organic solvent, the extract is salified with hydrochloric acid. The target product Memantine Hydrochloride is collected. The yield can exceed 69.5% and the product purity can exceed 99.0%.

Based on this invention, the re-crystallization solvent can be used to re-crystallize the said salt to yield Memantine Hydrochloride.

The urea-formic acid act as the reaction reagent of amination and the said formic acid is anhydrous formic acid or formic acid aqueous solution of various concentrations. The formic acid is also used as solvent.

The molar ratio between 1-bromo-3,5-dimethyl adamantane and urea and formic acid is preferably 1:2~5:5~10 and the reaction temperature is preferably 60-150° C.

The inorganic acid may be one selected from hydrochloric acid, hydrobromic acid, sulfuric acid, phosphoric acid or their mixture.

The inorganic base may be one selected from sodium hydroxide, potassium hydroxide, sodium carbonate, potassium carbonate, sodium hydrogen carbonate, potassium hydrogen carbonate or their mixture.

The organic solvent used for extraction may be one selected from hydrocarbon, ester, ether or their mixture.

The hydrocarbon may include benzene, toluene, xylene, cyclohexane, hexane, petroleum ether, etc.

The ester may include ethyl acetate, butyl acetate, etc.

The ether may include sulfuric ether, isopropyl ether, etc.

The re-crystallization solvent is preferably an alcohol such as methanol, ethanol, propanol, isopropanol, butanol and tertiary butanol, ketone such as acetone and butanone, water and mixtures of the foregoing.

This invention provides a new preparation method that uses low-cost and readily available raw materials, homogeneous phase and mild reaction conditions and simple post treatment, obtains high yield and high purity and is easy for mass production.

The method of this invention for preparing Memantine Hydrochloride provides the following advantages:

1. This invention makes some improvement based on the literature's method, such as adding formic acid to the mixture of 1-bromo-3,5-dimethyl adamantane and urea so that the reaction can be completed at a lower temperature and there is no need of tube sealing. The resulting product is homogenous without agglomerations and can be easily processed fruther. The method is easy to industrialize and creates advantages for mass production.
2. Due to the presence of formic acid in the aminating reaction, the product of 3,5-dimethyl adamantane is protected in the form of methanamide so to avoid oxidization, and the reaction solution maintains a light color. After the hydrolysis and salification, the purity of the yielded Memantine Hydrochloride crude can reach 99.0% and that of the re-crystallized product can reach 99.98% (see FIG. 1). The yield is 69.5% and the melting point is 332° C. (DSC), which is reported by 290-295° C. in the literature.

BRIEF DESCRIPTION OF THE DRAWING

The sole FIGURE is a GC spectrum of purified Memantine Hydrochloride.

DETAILED DESCRIPTION

EXAMPLE 1

Figure 1:
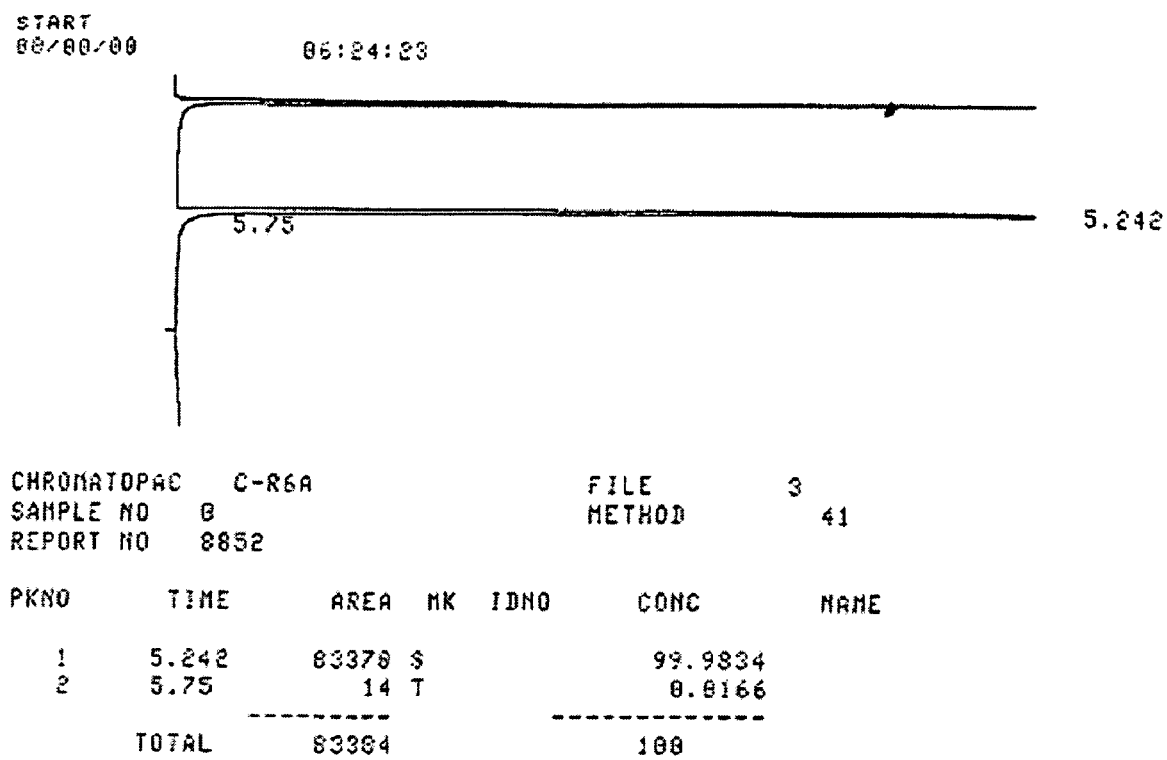

To 100 g of 1-bromo-3,5-dimethyl adamantane and 86 g of urea, adding 80 ml of 80 wt % formic acid, heating to 80° C. and holding for 3 hours. Cooling to the room temperature and adding 95 ml of concentrated hydrochloric acid to hydrolyze at 80° C. for about 1 hour. Adjusting with 30% sodium hydroxide to a pH of 12, extracting with toluene twice, combining the organic layers and washing with water. Concentrating under reduced pressure to yield a limpid yellow solution as the 1-amino-3,5-dimethyl adamantane crude. To the crude, adding 150 ml of ethanol and concentrated hydrochloric acid, heating to dissolve and crystallizing to yield white solid. Drying the solid and re-crystallizing with ethanol to yield 61.0 g of pure Memantine Hydrochloride. The yield of product is 68.8% (GC 99.5%).
$^1$HNMR (CDCl$_3$, 400 MHZ): δ0.833 (6H, singlet), 1.156 (2H, quartet), 1.328 (4H, quartet), 1.683 (4H, quartet), 1.869 (2H, broad signal), 2.179 (1H, broad signal), 8.28(3H, broad signal). MS (Q-Tof micro, ESI+): 179 (M$^+$), 164, 122, 108, 93 and 55. Element Analysis (C$_{12}$H$_{21}$N.HCl): actual results (calculated value %): C, 66.77(66.80); H, 10.40(10.28); N, 6.48(6.49); Cl, 16.39(16.43).

EXAMPLE 2

To 100 g of 1-bromo-3,5-dimethyl adamantane and 86 g of urea, adding 72 ml of 94 wt % formic acid, heating to 120° C. and holding for 2 hours. Cooling to the room temperature and adding 385 ml of 10% hydrochloric acid to hydrolyze at 100° C. for about 1 hour. Adjusting with 30% sodium hydroxide solution to a pH of 12, extracting with butyl acetate twice, combining the organic layers and washing with water. Concentrating under reduced pressure to yield a limpid yellow solution as 1-amino-3,5-dimethyl adamantane crude. To the crude, adding 150 ml of ethanol and concentrated hydrochloric acid, heating to dissolve and crystallizing to yield white solid. Drying the solid and re-crystallizing with water to yield 60.4 g of pure Memantine Hydrochloride. The yield is 68.1% (GC 99.1%).

EXAMPLE 3

To 100 g of 1-bromo-3,5-dimethyl adamantane and 10 g of urea, adding 60 ml of anhydrous formic acid, heating to 150° C. and hold for 1 hour. Cooling to the room temperature and adding 95 ml of concentrated hydrochloric acid to hydrolyze at 100° C. for 1 hour. Adjusting with 30% sodium hydroxide solution until the solution becomes basic. Extracting with toluene twice, combining the organic layers and washing with water. Concentrating under reduced pressure to yield a limpid yellow solution as 1-amino-3,5-dimethyl adamantane crude. To the crude, adding 150 ml of ethanol and concentrated hydrochloric acid, heating to dissolve and crystallizing to yield white solid. Drying the solid and re-crystallizing with acetone to yield 61.7 g of pure Memantine Hydrochloride. The yield is 69.5% (GC 99.9%).

EXAMPLE 4

To 100 g of 1-bromo-3,5-dimethyl adamantane and 86 g of urea, adding 80 ml of 80 wt % formic acid, heating to 80° C. and holding for 3 hours. Cooling to the room temperature and adding 75 ml of 85% phosphoric acid to hydrolyze at 80° C. for 1 hour. Adjusting with 10% potassium hydroxide aqueous solution to a pH of 12. Extracting with toluene twice, combining the organic layers and washing with water. Concentrating under reduced pressure to yield a limpid yellow solution as 1-amino-3,5-dimethyl adamantane crude. To the crude, adding 150 ml of ethanol and concentrated hydrochloric acid, heating to dissolve and crystallizing to yield a white solid. Drying the solid and re-crystallizing with ethanol to yield 61.0 g of pure Memantine Hydrochloride. The yield is 68.8% (GC 99.5%).
$^1$HNMR (CDCl$_3$, 400 MHZ): δ0.833 (6H, singlet), 1.156 (2H, quartet), 1.328 (4H, quartet), 1.683(4H, quartet), 1.869 (2H, broad signal), 2.179 (1H, broad signal), 8.28 (3H, broad signal). MS (Q-Tof micro, ESI+): 179(M$^+$), 164, 122, 108, 93 and 55. Element Analysis (C$_{12}$H$_{21}$N.HCl): actual results (calculated value %): C, 66.77 (66.80); H, 10.40 (10.28); N, 6.48(6.49) and Cl, 16.39(16.43).

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:
1. A method of preparing Memantine Hydrochloride comprising:
reacting 1-bromo-3,5-dimethyl adamantine, urea and formic acid at 50-180° C. for 0.25-5 h; adding inorganic acid aqueous solution and performing hydrolyzation at a pH of 1-3; adjusting with inorganic base aqueous solution until the reaction solution becomes basic; extracting with organic solvents; and salifying the extract with hydrochloric acid.
2. The method according to claim 1, wherein said ureaformic acid serves as reaction solvent for ammonization and said formic acid is anhydrous formic acid.
3. The method according to claim 1, wherein the molar ratio of 1-bromo-3,5-dimethyl adamantane, urea and formic acid is 1:0.5~10:1~15.
4. The method according to claim 3, wherein the molar ratio of 1-bromo-3,5-dimethyl adamantane and urea and formic acid is 1:2~5:5~10.

5. The method according to claim 1, wherein the hydrolysis temperature is from 50° C. to 100° C. and the duration is from 0.5 h to 5 h.

6. The method according to claim 1, wherein the inorganic acid is selected form hydrochloric acid, hydrobromic acid, sulphuric acid, phosphoric acid or a mixture thereof.

7. The method according to claim 1, wherein the said reaction solution is adjusted to a pH of 10 to 14 with an inorganic base and its aqueous solution.

8. The method according to claim 1, wherein the said inorganic base is selected from sodium hydroxide, potassium hydroxide, sodium carbonate, potassium carbonate, sodium hydrogen carbonate, potassium hydrogen carbonate or a mixture thereof.

9. The method according to claim 1, wherein the organic solvent used for extraction is selected from hydrocarbon, ester, ether or a mixture thereof.

10. The method according to claim 1, wherein Memantine Hydrochloride is obtained by recrystallizing the salt with recrystallizing solvent, and said recrystallizing solvent is selected from alcohol, ketone, water or a mixture thereof.

11. The method according to claim 1, wherein said urea-formic acid serves as reaction solvent for ammonization and said formic acid is formic acid aqueous solution.

12. The method according to claim 1, wherein the reaction temperature is from 60° C. to 150° C.

* * * * *